United States Patent
Pusillo

(10) Patent No.: US 10,772,344 B2
(45) Date of Patent: Sep. 15, 2020

(54) THERAPEUTIC AND NUTRITIONAL COMPOSITIONS

(71) Applicant: INTEQ, LLC, Overland Park, KS (US)

(72) Inventor: Gary Pusillo, Marshalltown, IA (US)

(73) Assignee: INTEQ, LLC, Overland Park, KS (US)

(*) Notice: Subject to any disclaimer, the term of this patent is extended or adjusted under 35 U.S.C. 154(b) by 0 days.

(21) Appl. No.: 16/234,992

(22) Filed: Dec. 28, 2018

(65) Prior Publication Data
US 2019/0313667 A1    Oct. 17, 2019

Related U.S. Application Data

(60) Provisional application No. 62/658,093, filed on Apr. 16, 2018.

(51) Int. Cl.
| | | |
|---|---|---|
| *A61K 38/01* | (2006.01) | |
| *A23K 10/18* | (2016.01) | |
| *A61K 38/18* | (2006.01) | |
| *A23K 20/147* | (2016.01) | |
| *A61P 25/22* | (2006.01) | |
| *A23K 50/20* | (2016.01) | |
| *A23K 50/10* | (2016.01) | |
| *A23K 50/40* | (2016.01) | |
| *A23K 50/60* | (2016.01) | |
| *A61K 31/7004* | (2006.01) | |

(52) U.S. Cl.
CPC ............. *A23K 50/20* (2016.05); *A23K 10/18* (2016.05); *A23K 50/60* (2016.05); *A61K 31/7004* (2013.01); *A61K 38/018* (2013.01); *A61K 38/18* (2013.01); *A61P 25/22* (2018.01)

(58) Field of Classification Search
None
See application file for complete search history.

(56) References Cited

U.S. PATENT DOCUMENTS

2017/0333537 A9* 11/2017 Borodic ............. A61K 38/4893

OTHER PUBLICATIONS

Aluthge, N. D. et al. "Board Invited Review: The pig microbiota and the potential for harnessing the power of the microbiome to improve growth and health" Downloaded from https://academic.oup.com/jas/advance-article-abstract/doi/10.1093/jas/skz208/5524612, Jul. 19, 2019, pp. 1-39.
Bornaz, S. et al. "Physicochemical properties of fermented Arabian mares' milk" *International Dairy Journal*, 2010, pp. 500-505, vol. 20.
Chiavari, C. et al. "Use of donkey's milk for a fermented beverage with lactobacilli" *Lait*, 2005, pp. 481-490, vol. 85.
Gubic, J. M. et al. "Microbiological, Chemical and Sensory Properties of Domestic Donkey'S Milk from Autochthones Serbian Breed" *Journal of Food and Nutrition Research*, 2014, pp. 633-637, vol. 2, No. 9.
Surono, I. S. et al. "In vivo Antimutagenicity of Dadih Probiotic Bacteria towards Trp-P1" *Asian Australasian Journal of Animal Sciences*, Jan. 2009, pp. 119-123, vol. 22, No. 1.

* cited by examiner

*Primary Examiner* — Sarvamangala Devi
(74) *Attorney, Agent, or Firm* — Saliwanchik, Lloyd & Eisenschenk

(57) ABSTRACT

Novel nutritional compositions and methods for their manufacture, administration and use are disclosed. The nutritional compositions of the present invention are useful for the feeding of immature mammals, particularly those used for food, and/or performance animals, such as horses, and for companion animals, such as dogs and cats. The nutritional compositions and supplements of the present invention are effective in supporting the growth and health of the immature mammal, in supporting and stimulating its immune system, and in mitigating undesirable infections and other. Additionally, particular fractions of the unique peptides produced by the disclosed methods can be separated and utilized as therapeutic agents.

11 Claims, No Drawings

THERAPEUTIC AND NUTRITIONAL COMPOSITIONS

CROSS-REFERENCE TO RELATED APPLICATION

This application claims the benefit of U.S. Provisional Application Ser. No. 62/658,093, filed Apr. 16, 2018, the disclosure of which is hereby incorporated by reference in its entirety, including all figures, tables and amino acid or nucleic acid sequences.

FIELD OF THE INVENTION

The present invention relates to nutritional compositions for enhancing health and development in domestic animals. The nutritional products and supplements are prepared by unique milk fermentation processes.

BACKGROUND OF THE INVENTION

Fermentation processes are used throughout the world for the manufacture of foods based on milk from a number of different mammalian sources, including domestic as well as wild animals. These processes typically involve adding lactic acid-producing microorganisms, such as bacteria and yeast to milk, which ingest lactose, or milk sugar, and release lactic acid as waste. Depending on fermentation conditions and milk source, different products are obtained.

Traditional uses of fermented mare's milk are believed to have beneficial effects in relief of metabolic and intestinal problems, gut-cleansing effects coupled with repair of intestinal flora, relief from stomach ulcers, and normalization of blood pressure, cholesterol and liver problems. It has been recommended as an aid in cancer treatment, likely due to enhanced nutrition and support of the immune system.

More recently, researchers have utilized fermented equine milk for the treatment of certain human pathologies, such as hepatitis, chronic ulcer and tuberculosis (Nassal and Rembalski, 1980; Solaroli, Pagliarini and Peri, 1993).

Fermentation agents are typically lactic acid bacteria, such as *Lactococcus lactis* subsp. *lactis*, *Lactococcus lactis* subsp. *cremoris*, *Lactococcus lactis* biovar *diacetylactis*, and *L. acidophilus*, and yeasts, such as *Leuconostoc mesenteroides*, subsp. *cremoris*. Mixtures of bacteria and/or yeast are used for many different products, including *Lactobacillus bulgaricus* and *Streptococcus thermophilus* for yoghurt, and a mixture of bacteria and yeasts for kefir and kumis.

Since ancient times, agrarian cultures have utilized milk for nutrition. Due to a lack of preservation methods and modern methods, such as refrigeration, yeast fermentation was typically used to provide a product that could be safely used over a period of time. However, the fermented milk products differed in quality and characteristics depending on the milk source. Production methods were not controlled and depended on naturally occurring yeasts and bacteria already present in the milk.

Even today in the human populations of central Asia and the former Soviet Union, fermented horse milk is mainly used for the manufacture of a lactic-alcoholic beverage containing from 2-5% alcohol, known as Airag or Koumiss. Typically, the fermentation bacteria utilized are lactic acid bacteria, such as *Bifidobacterium mongoliense* sp., *Lactobaccilus heveticus* and *Lactobacillus kefiranofaciens*. Surono and Hosono (2003) disclose a combination of *Lactobacillus lactis* subsp. *Lactis*, *Lactobacillus delbrueckii* subsp. *bulgaricus* and the yeast *Torula* spp. for the production of Koumiss.

Commercially produced fermented products for human consumption include cheese, sour cream, yoghurt and similar products in countries throughout the world, which are known as dahi (Pakistan), kefir (Russia), and créme fraiche (France). Differences between these food products arise from the use of milk with different milk fat contents and the fermentation agent. In many cases the bacteria and/or yeast are unknown or are already present in varying degrees in the collected milk. Some products are consistent in quality after controlled manufacture, e.g., sour cream, but have a short shelf life due to continuing action of the bacteria and/or yeast, e.g., créme fraiche, which has a typical shelf life of 10 days at 4° C. while sour cream has a shelf life of 4 weeks. Cheese exhibits a wide variation depending on milk source and milk fat content, which can range for 1 to 75% milk fat.

In addition to human food, animals have been fed different fermented feeds, traditionally produced by yeasts naturally present in grass crops that have been stored under moist conditions. Dairy farms have supplemented animal diets with rumen-specific live yeast, typically *Saccharomyces cerevisiae* (CNCM 1-1077), to improve subacute rumen acidosis in cows.

Interest has focused recently on animal feed efficiency and the value of fermented animal fodder for improving animal health and development. Fermented liquid feed for pigs was shown to increase weight 3-5% by using lacto-fermented feedstock (*J. Animal Science and Biotechnology*, 2015, 6-4). Fermented liquid feed can be produced from agricultural foodstock mixed with water, lactic acid bacteria and yeasts. The pH of liquid feed can be reduced so that stomach pH more efficiently inhibits proliferation of pathogens in the animal.

Nutritional benefits of milk alone are well recognized. Although mammalian milk is comparable in different species, equine milk naturally has better nutritional value than bovine milk.

Horse milk is superior to bovine milk in several characteristics, including: (1) more thermostable whey proteins; (2) less sensitivity to thermal processing; (3) lower casein content; (4) characterization as an albuminous milk; (5) ability to transmit in-utero chemosensory information relative to future food and "additive" products; (6) contains cathelicidins that work like natural antibiotics; (7) equal amounts of β-casein and α-casein; (8) contains N-acetyl-neuraminic acid (sialic acid) with a high concentration of 0-acetylation at position 4; (9) higher concentrations of lactoferrin and lysozyme; and (10) lysozyme is about 10% compared to trace amounts of lysozyme in bovine milk.

Tables 1-4 illustrate some of the differences in composition between horse and bovine milk.

Table 1 shows the differences between mare's milk and bovine milk.

TABLE 1

| Parameter | Equine Milk | Bovine Milk |
|---|---|---|
| Crude protein (g/kg) | 21.4 | 32.5 |
| True whey protein (g/kg) | 8.3 | 5.7 |
| Casein (g/kg) | 10.7 | 25.1 |
| NPN x 6.38 (g/kg) (non-protein nitrogen) | 2.4 | 1.7 |
| True whey protein (%) | 38.79 | 17.54 |
| Casein (%) | 50.00 | 77.23 |
| NPN x 6.38 (%) | 11.21 | 5.23 |

TABLE 1-continued

| Parameter | Equine Milk | Bovine Milk |
|---|---|---|
| Total solids (g/kg) | 110.0 | |
| Lactose (g/kg) | 63.7 | 48.8 |
| Fat (g/kg) | 12.1 | 36.1 |
| Ash (g/kg) | 4.2 | 7.6 |
| Gross energy (kcal/kg) | 480.0 | 674.0 |

Table 2 compares the lipid concentration of mare's milk and bovine milk.

TABLE 2

| Parameter | Equine milk | Bovine milk |
|---|---|---|
| Fat (g/kg) | 12.1 | 36.1 |
| Triglycerides (%) | 81.1 | 97.0 |
| Phospholipids (%) | 5.0 | 1.5 |
| Unsaponifiable (%) | 4.5 | 1.5 |
| Free Fatty Acids (%) | 9.4 | Trace |
| Palmitic FA (%) | 23.8 | 29.5 |
| Oleic FA (%) | 19.1 | 26.3 |
| Linoleic FA (%) | 9.6 | 2.9 |
| Linolenic FA (%) | 9.4 | 1.1 |
| Saturated FA (%) | 55.8 | 68.0 |
| Unsaturated FA (%) | 44.2 | 32.0 |

Table 3 compares the vitamin and mineral content of mare's milk and bovine milk.

TABLE 3

| Parameter | Equine milk | Bovine milk |
|---|---|---|
| Calcium (mg/L) | 500-1,300 | 1,100 |
| Magnesium (mg/L) | 40-110 | 100 |
| Zinc (mg/L) | 0.9-6.4 | 4 |
| Vitamin E (mg/L) | 0.26-1.13 | 0.6 |
| Riboflavin (mg/L) | 0.37 | 1.83 |

Table 4 shows the differences in casein species and micelle size between mare's milk and bovine milk.

TABLE 4

| Parameter | Equine milk | Bovine milk |
|---|---|---|
| Casein (g/kg) | 10.70 | 25.10 |
| $\alpha_s$ - casein (%) | 46.65 | 48.46 |
| $\beta$ - casein (%) | 45.64 | 35.77 |
| $\kappa$ - casein (%) | (7.71) | 12.69 |
| Micelles size (nm) | 255.00 | 182.00 |

BRIEF SUMMARY OF THE INVENTION

The nutritional compositions of the present invention are effective in supporting the growth and health of immature mammals, particularly in improving and stimulating the immune system, and mitigating undesirable infections and other diseases that are commonly prevalent in the typical environment of the immature mammal. The formulations are designed for efficient administration to herds, as well as to individual animals. Certain components found in the novel nutritional compositions arise in part from the processing techniques which separate less desirable milk components and concentrate bioactive peptides which contribute to the nutritional and health benefits.

Particular fractions of the described fermented milk products can be separated and utilized as therapeutic agents; for example, for anti-anxiety activity in animals. This is particularly important in companion animals which commonly exhibit separation anxiety and noise-phobic behavior, in addition to benefiting modulation of the immune system and growth promotion.

The described compositions are typically prepared from mammalian milk and/or colostrum, which is fermented using a unique mixture of bacterial fermentation strains. Colostrum and/or milk components can be separated, and certain fractions can be utilized in new combinations to form nutritional compositions. These nutritional compositions comprise bioactive peptides which arise from changes the milk proteins have undergone during fermentation and processing.

The compositions of the present invention are formulated to enhance growth and strengthen the immune system in immature animals, particularly equine foals and other immature herd animals. Accordingly, the compositions are particularly useful as either a complement to, or substitute for key components of mammalian milk. The novel compositions promote cell maturation and support nutrient uptake during growth periods, as well as aiding in gut maturation. This ensures not only the health and growth of a neonate, but also the development of the actively growing young animal, maintenance of the adult, and enhancement of survivability and quality of life of mature or senior animals. The compositions promote uptake and increase the bioavailability of nutrients and production of required micronutrients.

An important aspect of the nutritional products of the present invention is the strengthening of the immune system which obviates common infections normally treated by antibiotics. The compositions will also assist in the protection of the intestinal mucosa from aggressive actions of potentially dangerous substances and pathogens and activate protective macrophages to fight infections and increase the immune system. They may scavenge free radicals that could damage cell tissue and reduce cell immunity. By protecting intestinal tissue, the compositions rebuild tissue damaged from chronic diarrhea, and prevent the return of the diarrhea condition and its resulting damage to intestinal tissue.

An advantage of the compositions of the present invention is the convenient manufacture under commercial conditions in large quantities. This makes sufficient quantities available for treatment of performance animals, such as horses and production animals, such as cattle, goats, and sheep, including companion animals in need of such nutritional support. The compositions of the present invention can be formulated for convenient administration to both individual animals and herds of animals.

Additional features of the nutritional formulations of the present invention include stability under a range of usage conditions and a commercially acceptable shelf life. Certain formulations can be developed that also do not require refrigeration by the user throughout the shelf life prior to usage.

The described invention utilizes isolated milk peptides and bioactive components in the formulations from fermented mare's milk and bovine colostrum. These compositions provide a natural defense against Irritable Bowel Syndrome (IBS) and Irritable Bowel Disease (IBD), and repair damaged tissue from the use of NSAIDs (aspirin, etc.) and other conditions that cause intestinal damage. The bioactive ingredients in the disclosed novel compositions are extremely important as a preventive of squamous and glandular ulcers in horses. Certain isolated peptides and bioactive products arising from the fermentation process can be formulated to have physiological effects, such as behavior modification.

DETAILED DESCRIPTION OF THE INVENTION

The present invention relates to compositions produced from mammalian milk or colostrum, using a process which includes fermentation under defined conditions with one or more unique strains of bacteria. The product can be used directly as a feed or supplement or fractionated into different components which contribute more significantly to nutritional value compared to unfermented milk or colostrum.

The novel compositions are particularly useful in enhancing growth and strengthening the immune system in immature mammals, such as neonatal foals, calves, lambs, kids, puppies, kittens, camelids, and other animals that depend on colostrum for survival and growth. Through the administration of these compositions to juvenile mammals, nutritional uptake, and hence growth and maturation, is optimized, as well as strengthening of the immune system, optimization of anabolic body-building pathways, and protection against a number of conditions affecting the health of the animal.

The described nutritional compositions comprise milk peptides and bioactive components separated from fermented mare's milk and bovine colostrum. These compositions provide a natural defense against Irritable Bowel Syndrome (IBS) and Irritable Bowel Disease (IBD). Use of the compositions repairs damaged tissue arising from use of NSAIDs (aspirin, etc.) and other conditions that cause intestinal damage. This is extremely important in preventing squamous and glandular ulcers in horses. Behavior modification has also been observed when the compositions are used to treat stress and anxiety in domestic and companion animals.

The compositions contain concentrated mixtures of novel peptides produced by the new multi-stage fermentation method, in addition to naturally-occurring milk proteins in untreated milk, but lack the deleterious components commonly found in fermented milk products.

Enhanced nutritional compositions can be obtained from fermentation of animal feedstock, such as fodder, grass, or grain by-products which are treated with a unique mixture of Przewalski bacteria, particularly one or more or mixtures of the strains *Ruminococcus flavefaciens* (ATCC Accession No. 49949), *Butyrivibrio fibrisolvens* (ATCC Accession No. 19171), and *Fibrobacter succinogenes* (ATCC Accession No. 51216). A liquid culture mixture of the bacteria can be applied to feedstock, which is then used directly as feed or as a feed additive.

An unexpected effect of one component produced by the described fermentation method is its anti-anxiety effect. A significant calming effect is observed when administered to animals in certain high-stress situations which can cause acute anxiety, e.g., anxiety, fear, or abnormal behavior having a sudden onset, such as a visit to a veterinarian or groomer, separation from family, kenneling, shows, loud noises, such as fireworks or thunderstorms, pet adoptions, new homes, new dog houses, carriers, or crate cages, exposure to vehicle rides, relocation, etc. The fractionated product can also be utilized as a preventive agent for animals that are undergoing shipment or other transfer where they could injure themselves as a result of being frightened and/or anxious.

Products are typically produced from pasteurized and defatted mammalian milk, preferably from mare's milk or colostrum because equine milk's natural nutritional value is superior to that of bovine milk. The milk or colostrum is optionally fermented with *lactobacillus* bacteria before combining Przewalski bacterial cultures and subjected to heat and enzymatic processing.

The Przewalski bacteria used in the process for making the described nutritional products were originally isolated and cultured from the feces of the Przewalski horse, *Equus ferus przewalskii*, which is considered to be the last truly wild horse in existence and even today survives only in limited zoo environments. This rare and endangered equine, the ancestor of today's domestic horse, originally existed on large numbers in the steppes along the Mongolia/China border. Today the animal is officially considered extinct because the last individual sighted was over 50 years ago.

Mammalian milk or colostrum, after fermentation with a Przewalski culture, or optionally with lactic acid bacteria, preferably *Lactobacillus delbrueckii* subsp. *bulgaricus*, and *Streptococcus thermophilus*, is subjected to enzymatic proteolysis in a series of incubation steps followed by separation procedures described herein, to afford various semi-purified fractions which concentrate bioactive components. Further fractionation yields unique nutritional compositions which have desirable nutritional effects. The nutritional and biological effects of the fractions isolated from the described fermentation process are different from the effects of unfermented milk fractions.

The components of the compositions of the present invention provide nutritional supplementation for immature mammals and all mammals in need of the unique bioactive peptides critical for optimized health, growth and performance. These compositions enhance efficient growth, provide bioactive components that enhance, support and stimulate a neonate's growth and optimized differentiation of muscle groups, and/or strengthen and modulate the immune system, while providing basic and limiting nutrients to the neonate, rapidly maturing individual or animals requiring precise targeted bioactive nutrients that are typically rare and unavailable to a normal population of the same species.

The present invention also makes compromising environmental conditions less likely to negatively affect animals that consume the bioactive ingredients on a regular basis. The invention evens out the effect of an inconsistent or ever changing environment by providing the naturally rare concentrations of glyconutrients, bioactive peptides, immunoglobulins, sialic acid with the o-acetylation at position 4, cytokines, proline rich polypeptides, thymosin subunits, lactoferrin, transferrin, xanthine oxidase, lactoperoxidase, insulin-like growth factors, glutathione precursors, beta-lactoglobulins, alpha-lactoglobulins, lysozymes, beneficial microbials and prebiotics. In addition to these there are hundreds of metabolites and peptides that are derived from the fermentation of the mare's milk with the very rare inoculants (bacteria) which were isolated from the Przewalski horse.

The nutritional compositions of the present invention may also optionally include one or more ingredients to enhance the nutrition of the immature mammal, e.g., the equine foal, bovine calf or ovine lamb. Such ingredients may include vitamins and/or mineral supplements. For example, vitamin E can be added to the supplement, as can various minerals, such as selenium, copper, manganese, zinc, and/or chromium. In certain instances, it may also be desirable to include enzyme supplements to aid in digestion.

Other ingredient(s) of the nutritional product may include vitamins and minerals which contribute to the final nutritional product in their capacity as antioxidants and/or enhance the total nutritional qualities of the nutritional product. One of the additional ingredients used in a preferred embodiment is Vitamin E. Other ingredients may be used in the preferred embodiment, including various minerals, such as selenium, copper, manganese, zinc, and chromium. Especially for equines it may be desirable to include mannan oligosaccharides, typically those derived from the cell wall of the yeast *Saccharomyces cerevisiae*, and various supplemental dietary enzymes which are known to assist in aiding digestion of the grain-based diets commonly fed to mammals, especially horses. Typical enzyme supplements are those supplying bacterial *Bacillus licheniformis* alpha-amylase, alone or in combination with amyloglucosidase (AMG, another starch-digesting enzyme found in the small intestine), which are known to improve starch digestion in the horse.

*Echium plantagineum* seed oil (echium oil) is a terrestrial plant source that may hold promise as a sustainable alternative to fish oil because it has a very high content of unsaturated fatty acids (92% of total fatty acids; 50% of which are ω-3 FA), and is rich in stearidonic acid (15-20%) and gamma-linolenic acid. Stearidonic acid (SDA, C18:4 n3), a precursor of the bioactive lipids eicosapentaenoic acid (EPA) and docosahexaenoic acid (DHA) which are found in fatty cold-water fish. These acids are recognized as having possible functions to improve metabolism and delay the onset or prevent diabetes. Research in mice has found that echium oil improved glucose handling in the body. This is significant insofar as there are currently 84 million Americans who have prediabetes (1 in 3).

Use of echium oil and the bioactive peptide blends will improve glucose homeostasis, suggesting that combinations may (1) enhance systemic glucose uptake and possibly B-cell function, (2) lead to reduced visceral adipose accumulation, and (3) increase tissue PUFA accumulation while reducing tissue saturated fatty acid (SFA) accumulation.

Combinations of camel milk and echium oil are proposed as an alternative intervention for diabetes in humans and animals. The novel peptides produced by fermentation of bovine colostrum as described herein are alternative substitutes to camel milk.

Echium oil and the novel peptides produced by fermentation of bovine colostrum are showing promise as a novel and safe intervention in horses with Equine Metabolic syndrome (EMS), insulin dysregulation, and diabetes mellitus. By changing the concentration and ratios of ingredients it is possible to intervene in horses that have problems with EME related laminitis. EMS and pituitary pars intermedia dysfunction (also known as equine Cushing's disease), which also causes regional adiposity, laminitis, and sometimes insulin resistance, can be managed successfully with combinations of selected peptides and echium oil.

The combination of the ingredients discussed above in the preparation of the nutritional composition of the present invention for immature mammals will enhance both the growth and immunity of the animals, and result in healthy, productive and performance oriented adult animals, with a more defined easily obtainable quality of life when allowed to have optimized environmental conditions. The nutritional composition complements and compensates for deficiencies in the mother's milk, neonatal diets, and challenging environmental conditions, while also providing the rare bioactive substances that aid in protection from potentially dangerous pathogens in the feedstuffs available in the mother's and neonate's feed or forage.

The nutritional product of the present invention can be administered in any of a number of ways, including adding to feed, or fed directly as a nutritional composition. It is desirable that the immature mammal is given regular doses of the nutritional composition, typically daily or twice daily, for periods of 1-60, preferably 1-30, days after birth.

The nutritional composition of the present invention may be manufactured as a liquid or paste and stored in a gelatin capsule (as a gelcap), which provides a consistent dosage of the nutritional product. Alternately, it can be manufactured as a paste for oral administration using a dose syringe. Finally, it may be manufactured pelleted together with grass meal and/or alfalfa meal. The pelleting procedure should be performed at low temperature, preferably not higher than 65° C. The ingredients mentioned above should be approximately 5-60 percent, and, most preferably, about 20 percent, by weight of the pellet formulation.

The present invention teaches a nutritional product which enhances growth, while modulating and strengthening the immune system in neonates and animals that will directly benefit from the invention's rare and unique compilation of nature's most profoundly influential bioactive substances. As such, the nutritional compositions of the present invention are usable as either a complement to or substitute for mother's milk and a neonatal first diet other than mother's milk. It promotes proper cell maturation and metabolism while supporting nutrient absorption and assimilation during growth periods, homeostasis challenges, performance activities, as well as aiding in gut adaptation, maturation, and differentiation, and ensuring the health, growth, and quality of life of the immature, growing and mature mammal. It helps carry and increase the bioavailability of nutrients and help produce required micronutrients and further to sequence essential unidentified rare bioactive ingredients that have never been seen before in nature, but are created by nature and science coming together in the current invention.

More specifically, the nutritional compositions of the present invention also strengthen and modulate the immune system, and protect the intestinal mucosa from the aggressive actions of potentially dangerous substances and pathogens. These compositions activate protective macrophages to fight infections and boost the immune system, and scavenge free radicals that can damage cell tissue and reduce cell immunity. The nutritional compositions of the present invention also protect intestinal tissue, rebuild damaged tissue after chronic diarrhea, and prevent the diarrhea condition and the resulting damage to intestinal tissue. The oligosaccharide components of the compositions mimic lectin binding sites and prevent many pathogenic organisms from binding and causing damage.

The herein described nutritional products efficaciously treat and prevent digestive tract ulcers in foals and other immature animals. The invention is also effective in treating inflammatory bowel disease. The products consist entirely of safe and naturally derivatized ingredients rather than chemically manufactured drugs. The nutritional products of the present invention are administrable in a variety of dosage forms, thereby making their dispensation to both individual animals and herds a simple matter.

The nutritional product of the present invention is stable and has a long shelf life, and requires no special care to be provided by the user throughout its shelf life prior to usage.

The relative ranges of amounts of each of the components of the compositions, and their preferred amounts are discussed, beginning with the bioactive peptide component. The range of amounts of bioactive peptides is between approximately one-half percent and ten percent of the nutritional composition by weight. The preferred amount of the bioactive peptide component is approximately five percent of the nutritional product by weight.

The range of β-lactoglobulin is between approximately 30 and 70%, preferably about 40-60% of the nutritional product by weight. The most preferred amount of β-lactoglobulin is approximately 50-53% of the nutritional composition by weight.

The range of α-lactalbumin is between approximately 10 and 40%, preferably about 20-30%, of the nutritional composition by weight. The most preferred amount of α-lactalbumin is approximately 22-25% of the nutritional product by weight.

The preferred range of the amount of immunoglobulins is between approximately 10 and 30%, and more preferably about 14-25%, of the nutritional composition by weight. The most preferred amount of immunoglobulins is approximately 16-20% of the nutritional product by weight.

The preferred range of serum albumin is between approximately 2 and 10%, preferably about 3-8%, of the nutritional composition by weight. The most preferred amount of serum albumin is approximately 4-6% of the nutritional composition by weight.

The range of amounts of lactoferrin is between approximately 5 and 15 percent of the nutritional composition by weight. A preferred amount of lactoferrin is approximately 10 percent of the nutritional composition by weight.

The range of amounts of lysozyme is between approximately 10 and 11 percent of the nutritional composition by weight.

The range of amounts of Vitamin E is between approximately one-twentieth percent and one-half percent of the nutritional composition by weight. The preferred amount of Vitamin E is approximately two-tenths of a percent of the nutritional composition by weight.

The nutritional product of the present invention may be administered either by adding it to feed or by feeding it directly as a nutritional product. In a preferred embodiment, the nutritional product is administered once or twice daily. It may be manufactured either as a liquid, in which case it can be added to feed which is then fed to a horse, or as a liquid or paste and stored in gelatin capsules (as gelcaps), which makes for a consistent and uniform dosage of the nutritional product. If manufactured as a paste, it can also be orally administered using a dose syringe.

Alternatively, a nutritional product of the present invention may be manufactured by pelleting it together with grass meal and/or alfalfa meal. The pelleting procedure should be performed at a low temperature, preferably not higher than 65° C., to avoid the degradation or destruction of the beneficial ingredients, particularly those contained in the whey protein concentrate. The ingredients of the nutritional product should be approximately twenty percent by weight of the total weight of the pellets.

The typical dosage of the nutritional product of the present invention is approximately ten grams per day for foals from birth to three months old, approximately twenty grams per day for foals from three months to six months old, and approximately forty grams per day for foals from six months to a year old.

It will be readily apparent to those skilled in the art from the preceding discussion of the ingredients of the nutritional product of the present invention and their interaction that the benefits achieved by the nutritional product of the present invention is substantially greater than the sum of the benefits of each of the nutritional product's ingredients separately.

The description of the preferred embodiments of the present invention disclose nutritional products which both enhance growth and strengthen the immune system in equine foals and, potentially, in other animals and even humans as well. As such, the products of the present invention are usable as either a complement or substitute for mare's milk; promote cell maturation and support nutrient uptake during growth periods, as well as aiding in gut maturation and ensuring the health and growth of foals or young horses. The products help carry and increase the bioavailability of nutrients and helps produce required micronutrients.

The disclosed products strengthen the immune system and help protect the intestinal mucosa from the aggressive actions of potentially dangerous substances and pathogens; activate protective macrophages to fight infections and boost the immune system, and scavenge free radicals that could damage cell tissue and reduce cell immunity. The products also protect intestinal tissue, rebuild damaged tissue after chronic diarrhea, and prevent the diarrhea condition and the resulting damage to intestinal tissue.

The nutritional product of the present invention efficaciously treats and prevents digestive tract ulcers in foals and, potentially, in other animals and even humans. It consists entirely of safe and natural ingredients rather than drugs. The product is orally administrable, thereby making its dispensation a simple matter.

The nutritional products of the present invention are stable and have a long shelf life, and require no special care by the user throughout shelf life prior to usage. The products are also inexpensive relative to conventionally used nutritional products for foals, thereby enhancing market appeal and affording the broadest possible market. Finally, all the aforesaid advantages and objectives of the nutritional products method of administration are achieved without incurring any substantial relative disadvantage.

Materials

Mannan oligosaccharides (MOS) are derived from the cell wall of the yeast *Saccharomyces cerevisiae* (UK Vet Chem, Mulund West, Mumbai, Maharashtra, India).

INTIzyme enzymes (Integrated Laboratories PVT, Ltd, Shakti, Nagar, Ambala, Haryana, India) contain fungal diastase, pepsin and B complex. INTIzyme enzymes are a commercially available mixture of maltase, lactase, α-glucosidase, β-glucosidase, lipase, cellulose, protease and glycerophosphorase which facilitates the conversion of nutrient materials to sugars that are used for energy, amino acids which provide body building materials, and other materials, such as phosphoric acid, which provides regulatory functions within the animal, such as the maintenance of stable blood pH.

PRP is a proline-rich polypeptide mixture containing growth factors IGF-1 and 1111 IgG (DNA containing 6 tandem repeats affecting development). A PRP mixture is separated as a fraction from the fermented milk processed as described herein and contains about 25% ulin.

Przewalski culture is a culture medium or milk aerobically fermented with one or more of *Ruminococcus flavefaciens* (ATCC Accession No. 49949), *Butyrivibrio fibrisolvens* (ATCC Accession No. 19171), *Fibrobacter succinogenes* (ATCC Accession No. 51216) and *Ruminococcus albus* (ATCC Accession No. 27211).

"Bioactive Component 1" is a mixture of amino acids and peptides fractionated from milk or colostrum after fermentation with Przewalski bacterial cultures and processing with hydrolytic and proteolytic enzymes.

*Lactobacillus delbrueckii*, subsp. *bulgaris* (ATCC Accession No. 11842) and *Streptococcus thermophilus* (ATCC Accession No. 19528) are lactic acid bacteria used to ferment milk or colostrum.

Ingredient 1111 can be obtained from colostrum whey and provides b-lactoglobulin, a=lacctalbumin, albumin and immunoglobulins.

Echium oil is obtained from *echium plantagineum* plant seed and is available commercially (Jedwards International, Inc., Braintree, Mass.).

EXAMPLES

The present invention utilizes compositions that are prepared from mammalian colostrum and/or mammalian milk, using a fermentation process with Przewalski bacteria. The examples describe the compositions, processes for making the fermented products and beneficial effects of using the enhanced nutritional products.

Example 1

Przewalski Bacterial Cultures

The "Przewalski culture" used in the present invention is a mixture of one or more of bacterial strains which have been isolated from Przewalski horses. Fecal samples from Przewalski horses are inoculated onto agar and incubated in an anaerobic chamber at about 37° C. for about 40-60 hours. The resultant sub-cultured colonies are then plated onto MRS agar (available from Sigma-Aldrich). The MRS broth is then adjusted to about pH 2.0, 3.0, 4.0 or 5.0 by the addition of hydrochloric acid, resulting in isolates which are then plated and grown in pure culture on MRS agar for about 50 hours at about 37° C. The strains are purified into single cultures by plating.

The bacteria comprising the "Przewalski culture" as employed herein comprise a mixture of *Ruminococcus flavefaciens* (ATCC Accession No. 49949), *Butyrivibrio fibrisolvens* (ATCC Accession No. 19171), *Fibrobacter succinogenes* (ATCC Accession No. 51216) and Ruminococcus *albus* (ATCC Accession No. 27211). Each of these organisms is available from the American Type Culture Collection (ATCC), or other similar culture collections throughout the world. Alternatively, one or more of Przewalski bacteria may be used where indicated as Przewalski cultures in the disclosed formulations.

Example 2

Fermentation Mash

Oat fiber is sprayed with the Przewalski culture of Example 1 grown to about 7 to 9 log cfu in liquid culture under aerobic fermentation conditions. The resulting mixture is a mash containing about 1-3% of the bacterial strains. The mixture is dried and ground to produce a "Dried Fermentation Mash" additive to supplement up to 20% of an animal feed. Fermentation mash metabolites are activated in the gut of the treated animal and contribute to health and immune system benefits.

Alternatively, the mash is not dried but used directly as a liquid feed or added to conventional feed as a liquid.

Example 3

Preparation of Bioactive Peptide Mixtures

Fermentation of mammalian colostrum or milk, particularly equine colostrum or milk with the Przewalski culture results in a mixture which has an increased silylation rate compared to the silylation rates of the milk components prior to fermentation. Further enzymatic processing of the fermented milk, using a sequence of proteolytic enzymes and heating followed by ultrafiltration, provides filtrates which consist of concentrated peptides formed during the fermentation process. Bioactive peptides can then be separated from the other components of the fermented milk using chromatography and HPLC to obtain mixtures of peptides in the range of 6000 Daltons as described in Example 5.

Example 4

Preparation of Proline-Rich Polypeptide ("PRP") Solution 1 kg mare's milk is heated at 90° C. for 3 min, then inoculated with 10 g of *Lactobacillus delbrueckii*, subsp. *bulgaris* (ATCC Accession No. 11842) and *Streptococcus thermophilus* (ATCC Accession No. 19528) cultured in skim milk for 8 hrs at 42° C. to 9.0 and 7.0 log cfu mg/ml, respectively. The mixture is stirred, bottled and heated at 42° C. to a pH of 4.2. The mixture is cooled to 4-6° C. and can be stored for at least 45 days.

The milk is treated to remove lipids. The separated lipids, comprising fatty acids, glycolipids and phospholipids are removed from the colostrum or milk. The defatted milk contains immunoglobulins (IgG), proline-rich polypeptides, glycoproteins, oligosaccharides, enzymes, interferons, cytokines, bactalbumins, probiotic bacteria/microbiome/ growth factors and certain vitamins and minerals. Chromatography of the defatted milk provides a protein rich fraction rich in proline-rich polypeptides (PRP). This fraction is further fractionated to provide a "PRP" solution containing 70-100% proline-rich polypeptides.

Example 5

Method for Preparing Bioactive Component 1

Pasteurized and defatted colostrum or milk is fermented with the Przewalski culture of Example 1 and processed with rennet to precipitate casein. The filtrate containing lactoferrin, which has a molecular weight of about 80,000, is taken up in distilled water at 5% (wt/vol), and the pH is adjusted to about 2.5. This solution is then subjected to porcine and/or cod pepsin (EC 3.4.23.1, 10 units/mg) in acidic pH, followed by aspartic protease (PD enzyme) of *Penicillium duponti* at 10 units/mg at a temperature of about 37° C. for a period appropriate to the specific enzyme.

The resultant acidic pH enzymatically treated composition is then adjusted to a pH of 7.0, and incubated with protease A (10 units/mg, Amano Pharmaceutical); papain (EC 3.4.22.2, 50 units/mg, Nagase Biochemical Co.); Actinase AS (230 units/mg, Kaken Pharmaceutical Co.); trypsin (EC 3.4.21.4, 1000 units/mg, Sigma Chemical Co.) and Bioprase (20 units/mg, Nagase Biochemicals Co.). This hydrolysis reaction is conducted at a temperature of about 37° C. for a period appropriate to the specific enzyme.

The reaction is neutralized by the addition of 1N sodium hydroxide to stop further hydrolysis and/or any other enzymatic activity. Heating to about 80° C. for a period of about 10-60 minutes, preferably a period of about 15 minutes, stops further hydrolysis, leaving a composition containing approximately forty distinct bioactive peptides having a range of molecular weights of less than about 6000 kD. The degree of hydrolysis ranges from <1% to about 40% consisting of about 1% to about 35% free amino acids. These distinct bioactive peptides ("Bioactive Component 1") can be utilized as mixtures, and included as an ingredient in the herein-described nutritional products.

The Bioactive Component 1 mixture can be fractionated by conventional techniques, such as column chromatography, ultrafiltration, or combinations thereof, to produce pure or substantially pure bioactive peptide mixtures having varying molecular weights in the approximate range of <500 to about 10,000 daltons.

Example 6

Defatted equine colostrum can be treated with rennet, and precipitated casein removed by filtration, resulting in colostrum whey. The main components of colostrum whey are β-lactoglobulin, α-lactalbumin, albumin and immunoglobulins. These are typically separated by isoelectric point using ion exchange media in a stirred tank reactor Table 5 shows the relative proportions of the proteins and their isoelectric points.

A lactose solution is added to the colostrum solution. The diluted protein liquor is subjected to ultrafiltration and concentrated. Further nanofiltration/diafiltration can be used to isolate the various peptides shown in Table 5.

TABLE 5

| Component | Proportion (%) | Isoelectric Point |
|---|---|---|
| β-lactoglobulin | 50-53 | 5.2-5.4 |
| α-lactalbumin | 22-25 | 4.5-5.1 |
| Albumin | 4-6 | 4.9-5.1 |
| Immunoglobulins | 16-20 | 5.8-8.3 |

Example 7

Equine Nutritional Composition—Formula 1040

The ingredients shown in Table 6 are combined in dry form and thoroughly mixed. The composition is mixed with conventional feed or used separately and administered on a daily basis.

TABLE 6

| Ingredient | % by weight |
|---|---|
| Bioactive component I | 83.302 |
| INTIzyme enzymes | 10.433 |
| 1111, IGg 0.8676 g., PRP 4.338 mg, IGF-1 0.867 μg | 2.169 |
| Przewalski cultures | 2.272 |
| Mannan oligosaccharide | 1.824 |
| Total | 100.000% |

Five mature purebred quarter horses were fed daily with the nutritional composition added to regular feed as a supplement to provide about 15 to about 30 grams per animal, adjusted for the body weight and physical activity of the animal. Two horses were fed the same amount of feed without the supplement. Two horses did not have a measured control diet and were used as controls. The five horses receiving the supplemented feed showed at least 5% superior growth rates and better physiological health than the two horses receiving the same diet without the supplement and were also healthier than the two control horses.

This composition provides isolated milk peptides and bioactive ingredients that potentiate genetically predisposed capabilities for enhanced feed efficiency, improve fiber digestibility, allow phenotypic enhancement and allow growing animals to reach their genetic potential for muscle definition and function. The composition enhances anabolic metabolic agents in muscles; supplies agents that help the body to repair damaged tissue from the use of NSAIDs (aspirin, etc.) and other conditions that cause intestinal damage; prevents Irritable Bowel Syndrome (IBS) and Irritable Bowel Disease (IBD); supports intestinal integrity and helps reestablish epithelial health; optimizes support for multiple intestinal repair pathways and helps support a healthy gut barrier border, thereby contributing to overall immune health; reduces gut inflammation; resulting in a reduction of allergic symptoms; helps to partition aids in cell protection and increased proliferation of cell membrane protection components; and can aid in behavioral modification.

Example 8

Equine Nutritional Composition—Formula 1014

Table 7 shows the composition of a nutritional product particularly suited for maintenance of mature horses.

TABLE 7

| Ingredient | % by weight |
|---|---|
| 1111, IGg 17.62 g., PRP 88.1 mg, IGF-1 17.62 μg | 44.05 |
| MOS | 1.90 |
| Bioactive Component I | 41.85 |
| Przewalski Cultures | 2.20 |
| INTIzyme enzymes | 10.00 |
| Total | 100.00 |

This composition, when utilized at the described dosage, provides isolated milk peptides, eight essential saccharides and bioactive ingredients that potentiate genetically predisposed capabilities for enhanced feed efficiency; improve fiber digestibility; allows phenotypic enhancement and allows growing animals to reach their genetic potential for muscle definition and function; enhances anabolic metabolic agents in muscles; supplies agents that help the body to repair damaged tissue from the use of NSAIDs (aspirin, etc.) and other conditions that cause intestinal damage and squamous and gastric ulcers in horses; prevents Irritable Bowel Syndrome (IBS) and Irritable Bowel Disease (IBD); supports intestinal integrity and helps reestablish epithelial health; optimizes support for multiple intestinal repair pathways and helps support a healthy gut barrier border, thereby contributing to overall immune health; reduces gut inflammation resulting in a reduction of allergic symptoms; helps to partition nutrients to target tissues essential for proper immune function; enhances immune modulation; aids in cell protection and increased proliferation of cell membrane protection components; and can aid in behavioral modification, resulting in a decrease of many consequences of unwanted spontaneous activity. Further, it reduces inflammation and promotes healing in the performance horse and similar animal athletes and supports overall enteric health.

Example 9

Anxiolytic Composition

The active ingredient of the anxiolytic product is a decapeptide present in a low concentration in the Bioactive Component 1 mixture of Example 5. When the Bioactive component 1 mixture is fractionated using column chromatography, the decapeptide fraction can be purified to a level of about 70-100%, typically containing about 3-10 mg decapeptide/ml of liquid, Specific Gravity=0.99-1.11.

Optimal administration is 45 minutes to 1 hour prior to activity; for an acute situation, double the dose 1 hour before event. Stressful situations are unique to individual animals. Feeding levels can be increased with no risk. Shake container before each use. In general, 2 teaspoons for a 1200 lb. horse. Doses typically utilized in equines are shown in Table 8.

TABLE 8

PONIES & SMALL HORSES: 5 TO 10 mL (2 teaspoons = 10 ml)
AVERAGE SIZE HORSES: 10 TO 30 mL (2 tablespoons = 30 ml)
LARGE HORSES: 30 TO 50 mL For animals experiencing nondynamic environmental stressors that lead to death can be utilized to treat and/or prevent anxiety in both companion animals, such as dogs and cats, and production animals, such as cattle, goats and sheep, as well as equines.

Anxiolytic Composition

TABLE 9

| Active Ingredient | Amount/100 g formulation |
| --- | --- |
| Decapeptide hydrolysate of equine milk casein comprising αS1-casein, αS2-casein, β-casein, κ-casein 3-10 mg/ml solution | 8.5 g |
| Sialic acid | 1600-1750 mg |
| IGF-1 | 25-38 μg |
| Proline Rich Polypeptides ("PRP") solution | 2-3.5 g |

Microbial Standards

TABLE 10

| Microbial Standards | Typical | Method(s) |
| --- | --- | --- |
| APC | <5000 cfu/g | AOAC 986.33, 989.10 |
| Coliforms | Absent/g | AOAC 991.14 |
| Escherichia coli | Absent/g | AOAC 991.14 |
| Yeast and molds | <10 cfu/g | AOAC 997.02 |
| Salmonella | Absent/25 g | AOAC 989.13 |
| Listeria | Absent/25 g | AOACVIP 997.03 |
| Coagulase positive Staph. aureus | Absent/g | AOAC 2003.08 |

Chemical Standards

TABLE 11

| Chemical Standards | Typical | Method(s) |
| --- | --- | --- |
| Protein | 8.5% | AOAC |
| Fat | 1.4% | AOAC |
| Carbohydrates | 74.1% | Calculation |
| Ash | 14% | SMEDP |
| Moisture | 2% | AOAC |

A study was conducted using the anxiolytic composition to demonstrate the anti-anxiety effects on a group of 20 dogs. Within an hour of administration up to 90% of the dogs exhibited significantly reduced signs of stress or anxiety. 27% of the dogs were observed to be calmer within 20 minutes of administration. 86% of the dogs were observed to be calmer within 40 minutes of administration. 90%+ of the dogs were observed to be calmer within 50 minutes of administration.

In a similar study using cats, similar results were obtained with respect to the anxiolytic effects, and most importantly, a very low incidence of side effects was observed as compared to a placebo, with only about 4.45% of the anxyliotic compound treated cats exhibiting lethargy and a similar percent exhibiting excessive water intake. The placebo treated animals, in comparison, had 13.63% which exhibited "off feed/less intake", 9.09% exhibiting constipation, 4.45% exhibiting "not using litter box" and 9.09% exhibiting excessive water intake.

Example 10

Fermented Milk Preparation 1 kg mare's milk is heated at 90° C. for 3 min, then inoculated with 10 g of *Lactobacillus delbrueckii* subsp. *bulgaris* (ATCC Accession No. 11842) and *Streptococcus thermophilus* (ATCC Accession No. 19528) cultured in skim milk for 24 hrs at 40° to 45° C. to 9.0 and 7.0 log cfu/g, respectively. The mixture is stirred, bottled and heated at 42° C. to a pH of 4.2. The mixture is cooled to 4-6° C. and can be stored for at least 45 days.

Although the foregoing description of the nutritional compositions and the anti-anxiety compositions of the present invention have been shown and described with reference to particular embodiments and applications thereof, it has been presented for purposes of illustration and description and is not intended to be exhaustive or to limit the invention to the particular embodiments and applications disclosed. It will be apparent to those of ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. An anxiolytic composition for ameliorating stress or anxiety in a companion animal or a production animal, said composition comprising sialic acid, insulin-like growth factor 1 (IGF-1), a proline-rich polypeptide (PRP) solution comprising 70-100% proline-rich polypeptides, and a decapeptide hydrolysate of casein comprising αS1-casein, αS2-casein, βS2-casein and κ-casein, wherein the PRP solution is obtained by fermenting defatted mammalian milk with *Lactobacillus delbrueckii* and *Streptococcus thermophilus* and wherein the composition is in an amount sufficient to ameliorate the stress or the anxiety in said companion animal or said production animal.

2. The anxiolytic composition of claim 1, wherein the companion animal is a dog, equine, or cat.

3. The anxiolytic composition of claim 1, wherein the production animal is a cow, goat or sheep.

4. The anxiolytic composition of claim 1, wherein the composition upon administration to the companion animal or the production animal in amounts of 5 to 50 grams, 45 minutes to one hour prior to an acute situation, ameliorates the stress or the anxiety.

5. The anxiolytic composition of claim 4, wherein the acute situation is abnormal behavior having a sudden onset.

6. The anxiolytic composition of claim 5, wherein the acute abnormal behavior includes fear and reaction to loud noise.

7. The anxiolytic composition of claim 2, wherein the amount sufficient to ameliorate the stress or the anxiety in an equine is 10 to 50 grams depending on its size and age.

8. The anxiolytic composition of claim 7, wherein the amount sufficient to ameliorate the stress or the anxiety in an average sized 1200 pounds equine is 30 grams.

9. The anxiolytic composition of claim 1, wherein the proline rich polypeptide (PRP) is 2 to 4 weight percent, the sialic acid is 1.6 to 1.75 weight percent, the IGF-1 is 2.5 to $3.8 \times 10^{-4}$ weight percent and the decapeptide hydrolysate is 8 to 10 weight percent of the composition.

10. The anxiolytic composition of claim 9, wherein the decapeptide hydrolysate of casein is obtained by hydrolysis of casein precipitated from defatted equine colostrum.

11. The anxiolytic composition of claim 1, wherein the defatted mammalian milk is mare's milk.

* * * * *

UNITED STATES PATENT AND TRADEMARK OFFICE
CERTIFICATE OF CORRECTION

| | |
|---|---|
| PATENT NO. | : 10,772,344 B2 |
| APPLICATION NO. | : 16/234992 |
| DATED | : September 15, 2020 |
| INVENTOR(S) | : Gary Pusillo |

Page 1 of 1

It is certified that error appears in the above-identified patent and that said Letters Patent is hereby corrected as shown below:

In the Specification

Column 2,
Line 24, "(CNCM 1-1077)," should read --(CNCM I-1077),--.
Line 49, "0-acetylation" should read --O-acetylation--.

Column 7,
Line 32, "B-cell" should read --β-cell--.

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*